United States Patent [19]
Lyalin

[11] Patent Number: 5,803,737
[45] Date of Patent: Sep. 8, 1998

[54] PREFABRICATED TEMPORARY BRIDGE SYSTEM AND METHOD OF MAKING

[76] Inventor: Oleg Lyalin, 2078 E. 55th St., Brooklyn, N.Y. 11234

[21] Appl. No.: 915,486

[22] Filed: Aug. 20, 1997

[51] Int. Cl.[6] .................................................... A61C 5/10
[52] U.S. Cl. ........................................... 433/223; 433/181
[58] Field of Search ................................... 433/180, 181, 433/182, 183, 218, 223, 167

[56] References Cited

U.S. PATENT DOCUMENTS

| | | | |
|---|---|---|---|
| D. 338,529 | 8/1993 | Guthrie | D24/156 |
| 2,194,790 | 3/1940 | Gluck | 433/183 |
| 2,635,338 | 4/1953 | Dallenbach | 433/183 |
| 3,793,728 | 2/1974 | Corbiaeau | 433/183 |
| 4,269,595 | 5/1981 | Nemethy | 433/191 |
| 4,431,418 | 2/1984 | Kienhofer | 433/183 |
| 4,744,757 | 5/1988 | Adair et al. | 433/181 X |
| 4,764,116 | 8/1988 | Shoher | 433/180 |
| 4,957,439 | 9/1990 | Shoher et al. | 433/180 |
| 5,074,791 | 12/1991 | Shoher et al. | 433/180 |
| 5,458,489 | 10/1995 | Tennyson | 433/181 |

*Primary Examiner*—Nicholas D. Lucchesi
*Attorney, Agent, or Firm*—Goldstein & Canino

[57] ABSTRACT

A system for constructing temporary bridges to fill edentulous spaces found between a pair of abutment teeth in a human mouth is disclosed. The system contemplates selecting an appropriate prefabricated temporary bridge mold from a selection of pre-sized molds. The portion of the prefabricated temporary bridge mold which corresponds to the edentulous space and flanking abutment teeth is selected and cut away and retained as a mold subsection. The mold subsection is then filled with acrylic mix, and placed on top of the edentulous space and flanking abutment teeth such that the flanking abutment teeth form hollowed cavities in the cast temporary bridge which is formed upon the hardening of the acrylic mix. The hardened, cast temporary bridge is then removed from the mold subsection and, after adjustments are made, placed over the edentulous space and on top of the flanking abutment teeth, the temporary bridge receiving the abutment teeth into the hollowed cavities, thus creating a firm anchoring to hold the temporary bridge in place.

1 Claim, 5 Drawing Sheets

PREFABRICATED TEMPORARY BRIDGE SYSTEM AND METHOD OF MAKING

BACKGROUND OF THE INVENTION

The invention relates to a system which utilizes prefabricated, pre-sized molded shells in order to construct temporary dental bridges.

Dental bridge prosthodontics involve the restoration of one or more teeth and the replacement of one or more natural teeth with an artificial device. A bridge is used to replace at least one missing tooth and is supported by adjacent natural teeth. The bridge typically comprises a cast member which fills the edentulous space between a number of teeth, and is anchored by appropriate means to said adjacent abutment teeth.

The present day construction of bridges is time consuming and complex, and usually prefaced with the construction of a temporary bridge to provide the patient with convenience and comfort until the permanent bridge is assembled and installed (which usually entails a waiting period of several days if not weeks). Even the process of preparing and installing temporary bridges, however, proves time consuming, complex and more expensive than necessary. For instance, custom molds and impressions are obtained to construct a simple temporary bridge which may be removed in a matter of days. A cheaper, quicker and more simplistic system for the construction of temporary bridges is needed.

Various references found in the prior art disclose prefabricated dental pontic assemblies and connectors, but none of said references disclose a system possessing the ease and simplicity of the instant invention as will be disclosed hereafter. While these units may be suitable for the particular purpose employed, or for general use, they would not be as suitable for the purposes of the present invention as disclosed hereafter.

SUMMARY OF THE INVENTION

It is an object of the invention to produce a prefabricated temporary bridge system.

It is a further object of the invention to provide a prefabricated temporary bridge system which utilizes pre-sized molded shells in order to construct temporary dental bridges.

It is yet another object of the invention to provide a prefabricated temporary bridge system which allows a temporary bridge to be constructed more cost effectively and in less time than methods known and utilized heretofore.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
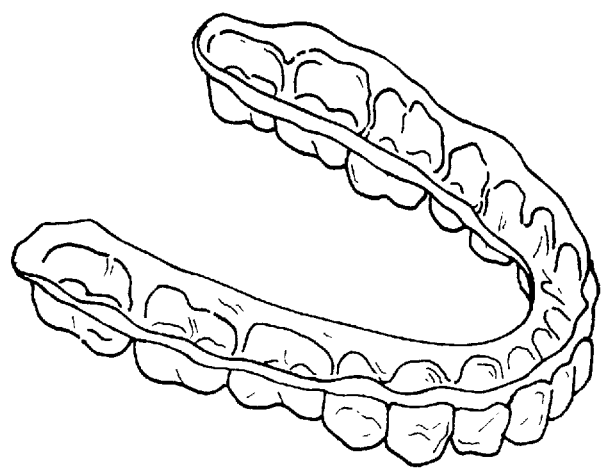
FIG. 1 is a diagrammatic perspective view of a prefabricated temporary bridge mold.
Figure 7:
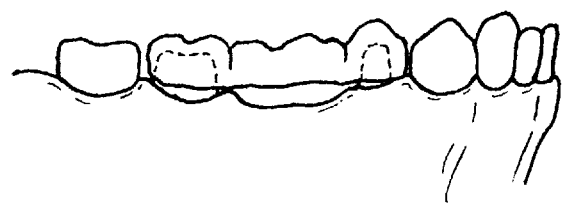
FIG. 7 depicts the temporary bridge installed within an oral cavity.

FIG. 1 illustrates a prefabricated temporary bridge mold 10 of the instant invention. Initial discussion of the prefabricated temporary bridge mold 10 will take place with reference to FIGS. 5 and 7 where a human mouth, and more particularly human gums 14 and teeth 16 are shown.

The instant inventive system provides a simple and inexpensive method for constructing a temporary bridge 20 to cosmetically and functionally improve a dental gap 22 (also known as edentulous space) found between a pair of teeth 16. Heretofore, the construction of a temporary bridge 20 involved taking a plaster impression of the patient's entire set of teeth, if they exist, and then creating a plastic mold through utilization of expensive impression machinery from said impression. The resultant mold was then used to create an exact-fitting temporary bridge. By providing pre-sized, pre-fabricated temporary bridge molds 10, the instant inventive system dispenses with the need to take plaster impressions of the patients set of teeth and then produce a mold therefrom.

Figure 4:
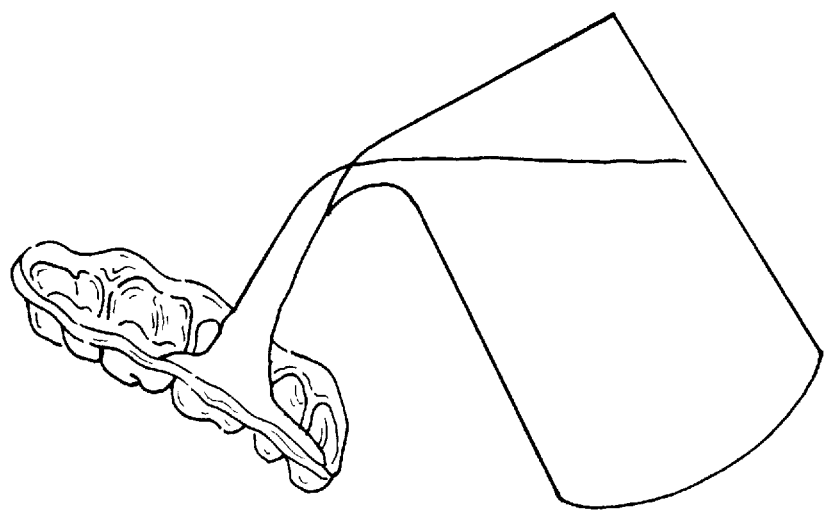
FIG. 4 depicts an acrylic mix being poured into the subsection of prefabricated temporary bridge mold in order to construct a temporary bridge.

The prefabricated temporary bridge mold 10 seen in FIG. 1 is horse-shoe in shape, and possesses a plurality of recesses 12 which, when filled with an acrylic liquid 18 such as that shown in FIG. 4, or other material capable of taking the shape of its surrounding container, produce a cast which represents a human tooth 12 or teeth.

Figure 2:
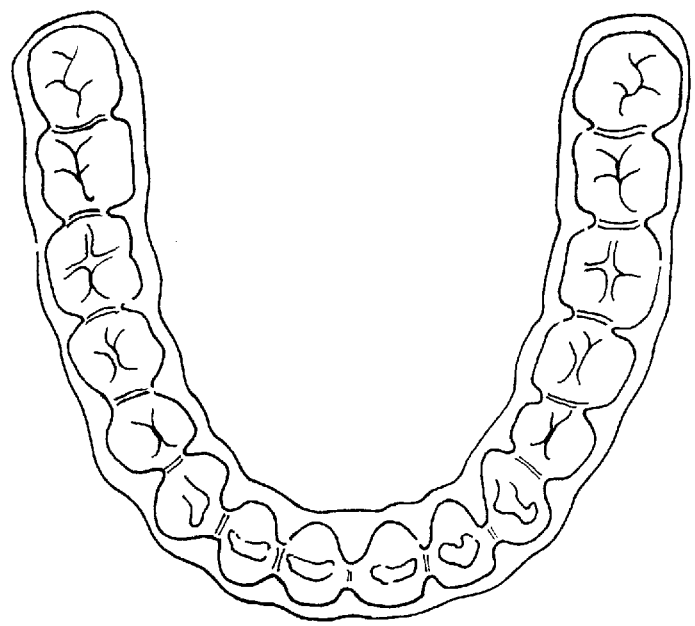
FIG. 2 is a top plan view of the temporary bridge mold of FIG. 1.

As seen in FIG. 2, exactly sixteen of said recesses 12 will comprise the prefabricated temporary bridge mold 10, as that is the number of teeth 16 present in a human mouth. In addition, the prefabricated temporary bridge mold 10 is configured to replicate a typical mouth in both tooth length and width as well as arch size. It is contemplated that the prefabricated temporary bridge mold be produced in approximately ten pre-set sizes in an attempt to replicate the most commonly found human arch shapes and tooth 16 lengths and widths.

Figure 3:
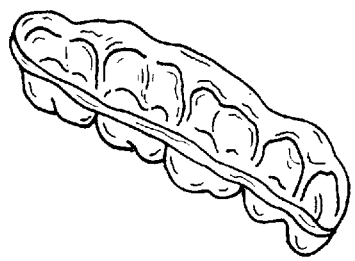
FIG. 3 is a subsection of the prefabricated temporary bridge mold.
Figure 5:
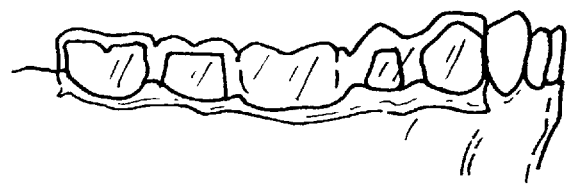
FIG. 5 illustrates the acrylic mix-filled subsection of prefabricated temporary bridge mold of FIG. 4 placed over a gap and adjacent teeth.

To employ the present inventive system, a measurement is obtained to determine the distance between the flanking adjacent teeth, and then one of a variety of supplied prefabricated temporary bridge molds 10 are chosen and placed upon the teeth 16 of the patient to assure that the mold 10 closest in size and shape is selected. Once chosen, a portion of that prefabricated temporary bridge mold 10 must be trimmed off for easier handling. For instance, FIG. 5 depicts a gap or edentulous space 22 in the posterior region of the right side of the mouth, said edentulous space 22 flanked on each side by abutment teeth 16A. Accordingly, the posterior portion of the prefabricated temporary bridge mold 10 which corresponds to the area where the edentulous space 22 and abutment teeth 16A are found would be trimmed off and utilized. The trimmed portion would accordingly comprise a mold subsection 24, as seen in FIG. 3.

Figure 6:
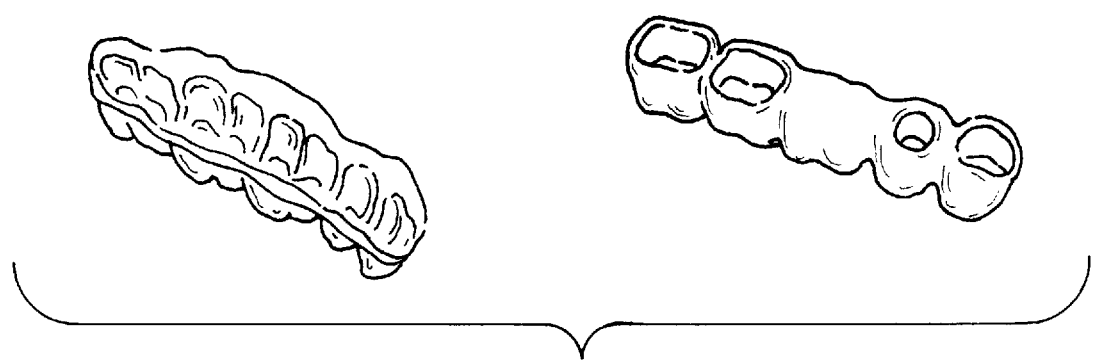
FIG. 6 depicts a hardened acrylic cast which comprises a temporary bridge, removed from the subsection of prefabricated temporary bridge mold.

The mold subsection 24 would then be filled with an acrylic mix 18 or other substance known to those well versed in the field to conform to the shape of a container and cure hardened therein. Once the acrylic mix 18 or other material was allowed to semi-harden within the mold subsection 24, said filled mold subsection 24 would then be placed on top of the edentulous space 22 and flanking abutment teeth 16A as seen in FIG. 5. At this point, the patient would close his or her mouth to assess the fit of the resultant cast temporary bridge 20, and any adjustments of acclusion, if needed, can be made. This action of placing the semi-hardened acrylic-filled mold subsection 24 on top of the edentulous space 22 and flanking abutment teeth 16A causes the flanking teeth 16A to form hollowed cavities 26 in the resultant cast temporary bridge 20 after it's removal from the mold subsection 24, as seen in FIG. 6. Subsequently, the temporary bridge 20 is placed over the edentulous space 22, and on top of the flanking abutment teeth 16A, receiving said adjacent teeth 16A into the hollowed cavities 26, creating a firm anchoring to hold the temporary bridge in place.

What is claimed is:

1. A method for constructing a temporary bridge which fills an edentulous space located between a pair of abutment teeth in a human mouth, the temporary bridge installed by anchoring it at each end to the abutment teeth which flank the edentulous space located therebetween; comprising the steps of:

a) obtaining a measurement between the pair of abutment teeth and then selecting a prefabricated temporary bridge mold from a group of various pre-sized molds, said selection also dependent upon choosing the prefabricated temporary bridge mold which best duplicates the size and configuration of the teeth located in the human mouth for which temporary bridge construction is intended;

b) locating a section of the temporary bridge mold which corresponds to the edentulous space and flanking abutment teeth, and cutting said section away from the remainder of the temporary bridge mold, said retained section comprising a mold subsection;

c) pouring a hardenable acrylic liquid mix into the mold subsection, said acrylic liquid to eventually harden into a cast temporary bridge;

d) waiting a pre-determined period of time sufficient for the acrylic liquid to cure into a semi-hardened state;

e) placing said acrylic filled mold subsection on top of the edentulous space and flanking abutment teeth such that the flanking abutment teeth form hollowed cavities in the cast temporary bridge;

f) removing the filled mold subsection from on top of the edentulous space and flanking abutment teeth, and waiting a further pre-determined period of time for the acrylic to cure into a hardened cast temporary bridge;

g) removing the hardened cast temporary bridge from the mold subsection, and performing adjustments to the length and width of said cast temporary bridge; and h) placing the removed, hardened cast temporary bridge over the edentulous space and on top of the flanking abutment teeth, the temporary bridge receiving said abutment teeth into the hollowed cavities, creating a firm anchoring to hold the temporary bridge in place.

* * * * *